United States Patent
Viñas et al.

(10) Patent No.: US 7,507,865 B2
(45) Date of Patent: Mar. 24, 2009

(54) METHOD FOR OBTAINING CALCIPOTRIOL HYDRATE

(75) Inventors: Antonio Buxadé Viñas, Barcelona (ES); Antonio Conchillo Teruel, Barcelona (ES); Carlos Mola Soler, Barcelona (ES)

(73) Assignee: Laboratorios Vinas, S.A. (ES)

( * ) Notice: Subject to any disclaimer, the term of this patent is extended or adjusted under 35 U.S.C. 154(b) by 0 days.

(21) Appl. No.: 12/005,698

(22) Filed: Dec. 28, 2007

(65) Prior Publication Data

US 2008/0167505 A1 Jul. 10, 2008

(30) Foreign Application Priority Data

Dec. 28, 2006 (ES) ................................ 200603291

(51) Int. Cl.
*C07C 35/21* (2006.01)
*C07C 35/22* (2006.01)

(52) U.S. Cl. ...................................... 568/816; 568/817

(58) Field of Classification Search ................. 568/816, 568/817
See application file for complete search history.

(56) References Cited

U.S. PATENT DOCUMENTS

| | | | | |
|---|---|---|---|---|
| 4,866,048 | A * | 9/1989 | Calverley et al. | ............ 514/167 |
| 5,763,426 | A * | 6/1998 | Hansen et al. | ............... 514/167 |
| 6,753,013 | B1 * | 6/2004 | Didriksen et al. | ............ 424/484 |
| 6,787,529 | B2 * | 9/2004 | Høy et al. | .................. 514/167 |
| 2007/0215455 | A1* | 9/2007 | Folkmann et al. | ...... 204/157.67 |

FOREIGN PATENT DOCUMENTS

WO WO9415912 * 7/1994

\* cited by examiner

*Primary Examiner*—Sikarl A Witherspoon
(74) *Attorney, Agent, or Firm*—Wood, Phillips, Katz, Clark & Mortimer

(57) ABSTRACT

Procedure to obtain the hydrate of calcipotriol. A procedure is described, used to obtain the hydrate of calcipotriol, which consists of the reaction of anhydrous calcipotriol in water, in the absence of organic solvents.

7 Claims, No Drawings

METHOD FOR OBTAINING CALCIPOTRIOL HYDRATE

FIELD OF THE INVENTION

The present invention refers to a procedure for obtaining calcipotriol hydrate crystals. Both calcipotriol and calcipotriol hydrate have been shown to be very useful as therapeutic agents in the treatment of psoriasis.

BACKGROUND OF THE INVENTION

Calcipotriol hydrate was described in *Acta Crystallographica*. Section C, Crystal Structure Communication, Col. C49, No. 3, 1993: 618-612, and in WO 94/15912 (ES 2111287) presents a procedure for obtaining the product from organic solvents and water. This method entails several difficulties:
- the organic solvents used must be removed afterwards, a disadvantage from an environmental point of view and contrary to "clean chemistry" practices;
- usable product yield is lost in the transformation, because part of it is left behind in the solvents or slurry;
- as with the majority of crystallized products in the presence of organic solvents, the end product usually contains residual organic solvents, a very important aspect, which is regulated in relation to the active pharmaceutical components.

SUMMARY OF THE INVENTION

The authors of the present invention, considering the state of the technology in regard to this subject, as stated in the preceding paragraph, discovered that, calcipotriol hydrate can surprisingly be obtained in a totally aqueous medium, free of organic solvents and with a nearly 100% useful yield.

The discovery of this process presents several advantages over the known state-of-the-art, which are directly related to the aforementioned surprising possibility of obtaining this product exclusively in water:
- not having to remove afterwards the slurry formed from the organic solvents;
- being able to obtain a product free from residual organic solvents;
- avoiding any loss of product yield during the process, given that there is 100% yield, which also entails an additional advantage, since there is no loss in a product of such high potency and toxicity in the slurry solvents, which must then also be eliminated or which would require recovery through an additional process.

According to the invention's process, anhydrous calcipotriol crystals are suspended in water and are left undisturbed, or preferably, agitated, during the time needed to be transformed into a hydrate (monohydrate) of calcipotriol. The hydration process can be controlled, if desired, by the ability to isolate the product when it has been partially hydrated, and to resume hydration by means of a new suspension and agitation in water. This process may be repeated as many times as necessary.

The time needed for total hydration may vary from a few hours to several days, depending on the size of the anhydrous calcipotriol crystals.

The process can be performed at temperatures between 0 and 100° C., but preferably in a range between 15 to 30° C.

The proportion of water can be vary between 1 to 200 parts of water per part of calcipotriol, but preferably between 50 to 100 parts of water.

The pH of the solution should preferably be kept above 7, preferably through the addition of ammonia or a low molecular weight anime: diethylamine, isopropylamine, triethylamine, etc.

Once the conversion of crystals is completed, they are isolated by known procedures, such as filtration or centrifuging, and, finally, the moisture or excess water is removed using known methods, such as vacuum drying.

Calcipotriol hydrate crystals obtained using this method can be used in medicine, for example, as anti-psoriasis agents.

The present invention is illustrated by, but not limited to, the following examples:

EXAMPLE 1

15.0 g of anhydrous calcipotriol were suspended in 150 mL of de-ionized water, 0.35 mL of concentrated ammonia were added and kept in agitation for 20 hours at 25° C. in an atmosphere of nitrogen. Afterwards, the product was filtered, left to drain, and vacuum-dried for 5 hours at 25° C.

The water content is analyzed by thermogravimetry [TG] and using a differential scanning calorimeter [DSC]. In some cases, replications of this experiment yielded water losses of less than 4%, although, in these cases, the isolated product was able to undergo the same process again until the hydration applicable to the hydrate was obtained.

Between 15.3 and 15.5 g of calcipotriol hydrate were obtained in this way.

EXAMPLE 2

10.0 g of anhydrous calcipotriol were suspended in 100 mL of de-ionized water, 0.25 mL of concentrated ammonia were added and kept in agitation for 12 hours at 40° C. in an atmosphere of nitrogen. Afterwards, the product was filtered, left to drain, and vacuum-dried for 5 hours at 25° C.

10.3 g of calcipotriol hydrate were obtained in this way.

EXAMPLE 3

15.0 g of anhydrous calcipotriol were suspended in 150 mL of de-ionized water, 0.35 mL of concentrated ammonia were added and kept in agitation for 50 hours at 25° C. in an atmosphere of nitrogen. Afterwards, the product was filtered, left to drain, and vacuum-dried for 5 hours at 25° C.

15.5 g of calcipotriol hydrate were obtained in this way.

Infrared Spectroscopy [KBr]

This shows a wide band at 3,600-3.100 cm$^{-1}$ and absorptions at 1,088, 1,061, 1,020, 965, 907, and 895 cm$^{-1}$.

Differential Scanning Calorimeter [DSC]

The loss of water was observed between 100 and 130° C., with an onset at around 116° C.

Thermogravimetry [TG]

This shows a loss between 4 and 5%.

The monohydrate corresponds to 4.2%, but, at times, the product is also obtained with a certain degree of moisture, in addition to the hydration water.

The invention claimed is:

1. Procedure to obtain calcipotriol hydrate consisting of making anhydrous calcipotriol react with water, in the absence of organic solvents, thus obtaining calcipotriol hydrate.

2. Procedure according to claim 1, characterized such that it includes a suspension stage of anhydrous calcipotriol in water, in the absence of organic solvents, and a stable stage of said suspension, during which the hydrate of calcipotriol is formed.

3. The procedure according to claim 2, characterized such that, after said stable stage, it includes a stage for separating the calcipotriol hydrate formed, a new stage for suspending anhydrous calcipotriol in water, and a new stable stage for said suspension.

4. Procedure according to either claims 2 or 3, characterized such that said stable stage is carried out a temperature ranging between 15° C. and 30° C.

5. Procedure according to any one of claims 1 through 3, characterized such that the proportion of water ranges between 1 and 200 parts of water per part of anhydrous calcipotriol, preferably ranging between 50 to 100 parts of water per part of anhydrous calcipotriol.

6. Procedure according to any one of claims 1 through 3, characterized such that the pH of the solution is held above 7.

7. Procedure according to claim 6, characterized such that ammonia or an amine of the group formed by diethylamine, isopropylamine, and triethylamine is added.

\* \* \* \* \*